United States Patent [19]

Schmitt-Willich et al.

[11] Patent Number: 5,759,518

[45] Date of Patent: Jun. 2, 1998

[54] METAL COMPLEXES OF DENDRIMERIC MACROMOLECULES, DIAGNOSTICS AGENTS THAT CONTAIN THE LATTER AS WELL AS PROCESS FOR THE PRODUCTION OF THE COMPLEXES AND AGENTS

[75] Inventors: Heribert Schmitt-Willich; Johannes Platzek; Andreas Muhler; Thomas Frenzel, all of Berlin, Germany

[73] Assignee: Schering Aktiengesellschaft, Berlin, Germany

[21] Appl. No.: 663,233

[22] PCT Filed: Dec. 2, 1994

[86] PCT No.: PCT/EP94/04016

§ 371 Date: Oct. 3, 1996

§ 102(e) Date: Oct. 3, 1996

[87] PCT Pub. No.: WO95/17451

PCT Pub. Date: Jun. 29, 1995

[30] Foreign Application Priority Data

Dec. 22, 1993 [DE] Germany ............ 43 44 460.1

[51] Int. Cl.$^6$ .......... A61B 5/055; A61K 51/04; A61K 49/04; C07F 5/00
[52] U.S. Cl. .......... 424/9.36; 424/1.65; 424/9.42; 424/9.364; 424/9.365; 534/10; 534/14; 534/15; 534/16
[58] Field of Search .......... 424/1.65, 9.322, 424/9.34, 9.341, 9.36, 9.364, 9.365, 9.4, 9.42; 534/10, 14, 15, 16; 540/465, 460

[56] References Cited

U.S. PATENT DOCUMENTS

| | | | |
|---|---|---|---|
| 4,587,329 | 5/1986 | Tomalia et al. | 528/363 |
| 5,135,737 | 8/1992 | Keana | 424/9 |
| 5,281,704 | 1/1994 | Love et al. | 540/465 |
| 5,364,613 | 11/1994 | Sieving et al. | 424/9 |
| 5,364,614 | 11/1994 | Platzek et al. | 424/9 |
| 5,405,601 | 4/1995 | Dunn et al. | 424/9 |
| 5,446,145 | 8/1995 | Love et al. | 540/465 |
| 5,449,761 | 9/1995 | Belinka, Jr. et al. | 534/10 |
| 5,517,993 | 5/1996 | Unger et al. | 128/653.4 |
| 5,527,524 | 6/1996 | Tomalia et al. | 424/1.33 |
| 5,556,968 | 9/1996 | Carvalho et al. | 540/460 |
| 5,593,660 | 1/1997 | Krause et al. | 424/9.451 |
| 5,650,136 | 7/1997 | Platzek et al. | 424/9.36 |

*Primary Examiner*—Gary E. Hollinden
*Assistant Examiner*—Michael G. Hartley
*Attorney, Agent, or Firm*—Millen, White, Zelano & Branigan, P.C.

[57] ABSTRACT

The invention relates to new metal complexes of dendrimeric macromolecules that contain 8 to 64 ions of an element of atomic numbers 21–129, 39, 42–44, or 57–83 and a polymeric, complexing ligand of formula I $$A-(X)_b \qquad (I)$$

in which A, X and b have different meanings, agents that contain these compounds as well as the use of the latter in diagnosis. The invention further relates to a process for the production of the complexes and agents.

12 Claims, No Drawings

METAL COMPLEXES OF DENDRIMERIC MACROMOLECULES, DIAGNOSTICS AGENTS THAT CONTAIN THE LATTER AS WELL AS PROCESS FOR THE PRODUCTION OF THE COMPLEXES AND AGENTS

The invention relates to the object characterized in the claims, i.e., new metal complexes of dendrimeric macromolecules, agents that contain these compounds, the use of the complexes in diagnosis as well as processes for the production of these complexes and agents.

Magnevist® (Gd-I)TPA/dimeglumine) is the first registered contrast medium for nuclear spin tomography (MRI= magnetic resonance imaging). It is especially well-suited for the diagnosis of pathological areas (e.g., inflammations, tumors, etc.). After intravenous injection, the compound is eliminated, through the kidneys; an extrarenal excretion is practically not observed.

A drawback of Magnevist® is that after intravenous administration, it is dispersed uniformly between the vascular space and the interstitial space. Thus, a delimitation of the vessels relative to the surrounding interstitial space is not possible.

For perfusion studies, a contrast medium is necessary, which is dispersed exclusively in the vascular space. Such a "blood-pool agent" makes it possible to delimit tissue that is well supplied with blood from tissue with insufficient blood supply with the aid of nuclear spin tomography and thus to diagnose an ischemia.

Other applications are vasography with the aid of nuclear spin tomography (so-called MR-angiography) and the graphic visualization of permeability disorders of blood vessels (such as, e.g., in malignant tumors).

So far, most patients in whom suspicion of a cardiovascular disease exists (this disease is the most -frequent cause of death in Western industrialized countries) have to undergo invasive diagnostic studies. In angiography, at present primarily diagnostic radiology with the aid of iodine-containing contrast media is used. These studies are associated with various drawbacks:

They are associated with the risk of radiation exposure as well as with difficulties and stresses, which are caused primarily by the fact that the iodine-containing contrast media, compared with NMR contrast media, have to be used at much higher concentration and do not remain in the vascular space.

There therefore exists a need for NMR contrast media, which can label the vascular space (blood-pool agent). These compounds are to be distinguished by good compatibility and by high effectiveness (high increase of the signal intensity with MRI).

The attempt to solve at least a part of these problems by using complexing agents, which are bound to macromolecules or biomolecules, has thus far been successful only to a very limited extent.

Thus, for example, the number of paramagnetic centers in the complexes, which are described in European Patent Applications 0 088 695 and 0 150 884, are not sufficient for satisfactory imaging.

Macromolecules are generally suitable as contrast media for angiography. 24 hours after intravenous injection in rats, however, albumin-Gd-DTPA (Radiology 1987; 162:205), e.g., shows a concentration in liver tissue, which constitutes almost 30% of the dose. Furthermore, only 20% of the dose is eliminated within 24 hours.

In EP 0 233 619, blood-pool agents based on polylysine-Gd-DTPA are described. These compounds are associated with the drawback, however, that only an unsatisfactory excretion of the complexes and thus of the heavy metal ions that are contained in the complexes is carried out.

The cascade polymer complexes that are described in EP 0 430 863 provided an improvement relative to the capability of excretion. Here, too, however, a complete excretion does not take place within a reasonable period, so that the danger of release of the metal from the complex exists.

Macromolecular contrast media that are based on carbohydrates, e.g., dextran, have also been described (European Patent Application 0 326 226). The drawback of these compounds lies in the fact that they generally carry only 4.6% of the signal-amplifying paramagnetic cation.

The object of this invention was therefore to find new diagnostic agents primarily to detect vascular diseases that do not have the above-mentioned drawbacks, i.e., to find metal complexes which, after intravenous administration within the period of study, show a low diffusibility through the vascular walls and nevertheless are quantitatively excreted.

This object is achieved by this invention.

It has been found that dendrimeric polymer complexes of formula I $$A\text{—}(X)_b \tag{I}$$

in which

A stands for a nitrogen-containing nucleus of base multiplicity b, whereby b means the sum of the free valences of the nitrogen-containing nucleus and stands for numbers 1 to 8 and X stands for a radical that consists of

reproduction units S and $2^n$ imaging radicals Y in which n determines the number of generations and stands for numbers 1, 2, 3 or 4, S stands for a radical of formula II

(II)

in which

R stands for a hydrogen atom or a methyl group and the positions

α for $0 \leq k \leq n-1$ are occupied by other reproduction units S, and for the nth generation by imaging radical Y of formula III or IV,

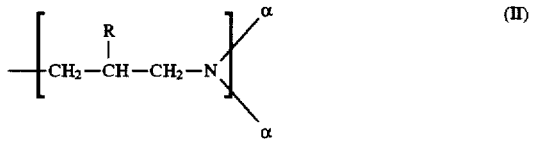

(III)

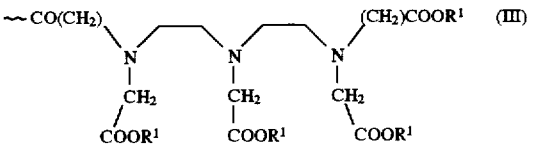

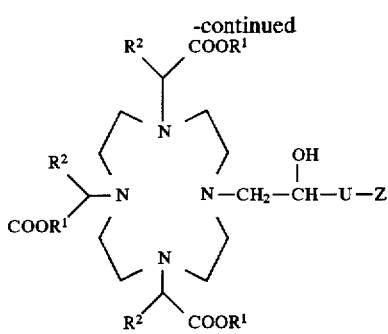
(IV)

in which

R¹, independently of one another, contain hydrogen or a metal ion equivalent of the elements of atomic numbers 21–29, 39, 42–44 or 57–83, R² stands for a hydrogen atom, a methyl or an ethyl radical, which optionally is substituted with 1–2 hydroxyl groups, U stands for a straight-chain, branched, saturated or unsaturated $C_1$–$C_{20}$ alkylene group that optionally contains imino, phenylene, phenylenoxy, phenylenimino, amide, hydrazide, carbonyl, ester groups; oxygen, sulfur and/or nitrogen atom(s), and that optionally are substituted by hydroxy, mercapto, oxo, thioxo, carboxy, carboxyalkyl, ester and/or amino group(s), and Z stands for a —CO, —NH—CO or —NHCS group, whereby the complexes contain at least 8–64 metal ions of the above-mentioned elements, and free carboxylic acid groups are present: optionally a salt of an inorganic or organic base or amino acid, are extremely well suited, surprisingly enough, as NMR diagnostic agents for contrasting the vascular space, without exhibiting the above-mentioned drawbacks.

The dendrimeric polymer complexes of this invention thus consist of a nucleus that contains 1 to 8 nitrogen atoms, whose free valences in the first generation are saturated respectively with a 3-aminopropyl group or a 3-amino-2-methyl-propyl group so-called reproduction units S.

A nitrogen atom, whose three free valences (basic multiplicity b=3) in the first generation are occupied by three reproduction units (or whose three hydrogen atoms of the basic ammonia are substituted by three reproduction units S), represents the simplest dendrimeric nucleus. Each of these three reproduction units contains a terminal nitrogen atom, whose (two) free valences either a) are completely saturated by the imaging radicals of formula III or IV, or b) are each occupied by another reproduction unit S.

In the case of the previously mentioned example of a nitrogen nucleus, this second generation consists of 6 (3×2) reproduction units with just as many terminal nitrogen atoms. The total 12 (6×2) free valences of the 2nd generation can now either a) be saturated by the imaging radicals of formula III or IV or b) be occupied repeatedly by identical reproduction units S, so that a third generation results. This 3rd generation can optionally be followed by a fourth.

According to the invention, dendrimeric polymer complexes that consist of at most 4 generations but at least one generation are suitable. In this case, the last (or nth) generation exhibits terminal nitrogen atoms, multiplied $2^1/2$ with basic multiplicity b, with $2^n$ α-positions, which are occupied completely with imaging radicals of formula III or IV. In this case, both the reproduction units and the imaging radicals within a molecule are identical.

The number of reproduction units that are contained altogether in the molecule is determined by the number of generations and calculated according to formula $$b \cdot \sum_{k=0}^{n-1} 2^k,$$

in which b stands for the basic multiplicity, n stands for the number of generations and k stands for a sequence number, which runs from 0 to n−1.

Thus, e.g., a polymer that consists of three generations (n=3) contains altogether $$b \cdot \sum_{k=0}^{3-1} 2^k [= b \cdot (2^0 + 2^1 + 2^2)] = b \times 7$$

identical reproduction units.

For the above-named case of the nitrogen nucleus with basic multiplicity b=3, altogether 21 (3×7) reproduction units S thus result. In addition, the polymer contains $b \times 2^n$ imaging radicals, in the actual case thus 24 (3×2³).

X thus stands for a branch of the dendrimeric polymeric complex, which consists of the sum of the reproduction units and related imaging radicals Y.

As cascade nuclei A, in principle any nitrogen-containing nuclei, with at most 8 free valences on the nitrogen atoms, are suitable. In addition to the above-mentioned nitrogen nucleus, there can be mentioned as examples a

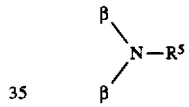

group or a β—N—$(R^5)_2$ group. Especially suitable, however, is a radical of general formula V, VI, VII, or VIII,

 (V)

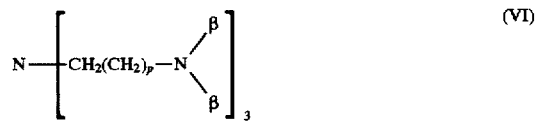 (VI)

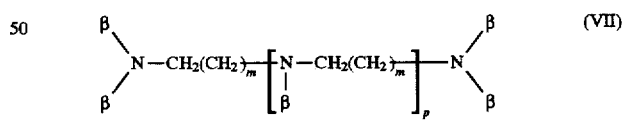 (VII)

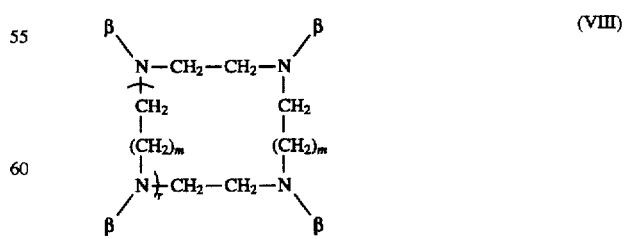 (VIII)

in which

R⁵ stands for an alkyl, aryl or aralkyl radical with up to 12 C atoms that is optionally substituted with 1–4 OH groups.

β marks the binding site to radical X, whereby the number of βs is to be equated to basic multiplicity b, W stands for a straight-chain or branched alkylene, arylene or aralkylene radical with up to 12 C atoms that optionally is interrupted by 1–4 oxygen atoms and/or substituted by 1–4 hydroxy groups, p stands for numbers 1 to 4, m, independently of one another, stand for numbers 1 or 2, and r stands for numbers 1 to 5.

As examples for the amines A(H)b on which cascade nucleus; A is based, there can be mentioned ammonia, tris-aminoethylamine, 1,4,7,10-tetraazacyclododecane (cyclene), 1,4,7,10,13,16-hexaazacyclooctadecane, 1,3-diaminopropane, 1,4-diaminobutane, 1,5-diaminopentane, 1,12-diamino-4,9-dioxadodecane, 1,4,8,11-tetraazaundecane, 1,5,8,12-tetraazadodecane, 1,5,9,13-tetraazatridecane, diethylenetriamine or triethylenetetramine.

Preferred among them are ammonia, tris(2-aminoethyl) amine, diethylenetriamine or cyclene, but especially 1,4-diaminobutane.

Basic multiplicity B follows from the number of nitrogen-hydrogen bonds of amine A(II)b that correspond to the respective nucleus. Thus, ammonia has a basic multiplicity of 3, the tris(2-aminoethyl)amine has a basic multiplicity of 6, the diethylenetriamine a basic multiplicity of 5 and the 1,4,7,10-tetraazacyclododecane a basic multiplicity of 4.

The production of the dendrimeric polymeric complexes of general formula I according to the invention is carried out by a dendrimeric polymer with terminal amino groups of formula IX, A—(X')$_b$ (IX)

in which

A and b have the meaning indicated in claim 1 and

X' stands for X, whereby in contrast to X for the nth generation, however, the i-positions are not occupied by imaging radicals Y, but by hydrogen atoms, being reacted with a reactive precursor of the complexing agent or imaging complex in an acylation or addition reaction and then —if a complexing agent is involved in the reactive precursor—being reacted with metal salts or metal oxides of the above-mentioned metals to the desired polymer-linked complex.

The amino group-containing dendrimeric polymers of formula IX that are used as starting compounds are produced as disclosed in WO 93/14147.

If dendrimeric polymeric complexes are to be obtained from imaging radicals of formula III, generally the monoanhydride of diethylenetriaminepentaacetic acid (J. Pharm. Sci., 68 (1979) 194) is used as reactive precursor. The latter is reacted to the corresponding amide-linked compounds analogously to the processes disclosed in DE 42 32 925.

This reaction is carried out in liquid phase in the presence of a base.

Suitable reaction media are, for example, water, polar solvents such as tetrahydrofuran, dioxane, acetonitrile, N-methylpyrrolidone, formamide, dimethylformamide, dimethylacetamide and the like or their mixtures. The reaction is carried out preferably at pH 8–10, i.e., by adding bases such as, e.g., sodium or potassium hydroxide or triethylamine, at temperatures of 0°–50° C., preferably at room temperature. For complete reaction, the procedure is performed preferably with a 2- to 3-fold excess of anhydride.

Then, the thus obtained complexing agents, in a way known in the art, are reacted with metal salts or metal oxides to the complexes according to the invention.

If, however, dendrimeric polymeric complexes are to be obtained from imaging radicals of formula IV, generally a compound of general formula X

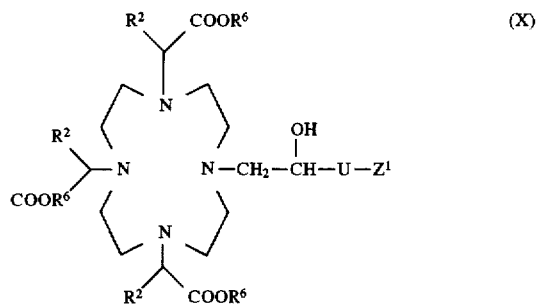

in which

R$^2$ has the indicated meaning and

U' stands for U or for a precursor of U,

R$^6$ stands for an acid protective group and/or means a metal ion equivalent and Z$^1$ stands for an isocyanate group, an isothiocyanate group, an activated acid group or a lactone radical, is used as a reactive precursor.

If R$^6$ stands for an acid protective group, the latter is cleaved in a way known in the art following the acylation or addition reaction, and the thus obtained compounds are reacted with metal oxides or metal salts to the complexes according to the invention.

As examples for an activated acid group, there can be mentioned as examples anhydride, p-nitrophenylester, N-hydroxysuccinimide ester, acid chloride and a carboxylic acid that is activated in situ by a carbodimide derivative.

As acid protective groups R$^6$, lower alkyl, aryl and aralkyl groups, such as, for example, methyl, ethyl, propyl, n-butyl, t-butyl, phenyl, benzyl, diphenylmethyl, triphenylmethyl, bis(p-nitrophenyl)-methyl or trialkylsilyl groups are suitable.

The cleavage of the acid protective groups is carried out according to processes known to one skilled in the art, for example, by hydrolysis, hydrogenolysis, alkaline saponification of esters with alkali in aqueous-alcoholic solution at temperatures of 0°–50° C., acid saponification with mineral acids or in the case of, e.g., tert-butyl esters with the aid of trifluoroacetic acid.

The acylation is carried out in liquid phase in the presence of inorganic and/or organic bases. Suitable reaction media are, e.g., tetrahydrofuran, dioxane, acetonitrile, formamide, DMF, DMSO, dimethylacetamide, water and the like or their mixtures.

Addition reactions of isothiocyanates with the desired amines of the dendrimeric polymer are generally carried out in polar solvents, such as, for example, water, alcohols, such as, e.g., methanol, ethanol or isopropanol, tetrahydrofuran, dioxane, acetonitrile, N-methylpyrrolidone, formamide, dimethylformamide, dimethylacetamide or their mixtures.

Analogous addition reactions of isocyanates are carried out preferably in anhydrous liquid phase according to processes known in the literature (Houben-Weyl, Methoden der Organischen Chemie [Methods of Organic Chemistry], Georg-Thieme-Verlag, Stuttgart, New York, Vol. E4 (1983), pp. 768–784).

The production of metal complexes from the complexing agents is carried out in such a way as has been disclosed in Patents EP 0 071 564, EP 0 130 934 and DE 34 01 052, by the metal oxide or a metal salt (for example, the nitrate, acetate, carbonate, chloride or sulfate) of the element of atomic numbers 21–29, 39, 42–44 or 57–83 being dissolved or suspended in water and/or a lower alcohol (such as methanol, ethanol, isopropanol and/or N,N-dimethylformamide) and reacted with the solution or suspension of the equivalent amount of complexing agent.

To achieve a physiological pH, acidic hydrogen atoms of acid groups ultimately can be substituted by cations of inorganic and/or organic bases or amino acids.

As bases, inorganic bases (e.g., hydroxides, carbonates or bicarbonates) of, e.g., sodium, potassium or lithium and/or organic bases, such as, i.a., primary, secondary and tertiary amines, such as, e.g., ethanolamine, morpholine, glucamine, N-methyl- and N,N-dimethylglucamine, as well as basic amino acids, such as, e.g., lysine, arginine and ornithine, are suitable.

For the production of neutral complex compounds, enough of the desired bases can be added, for example, to the acid complex salts in aqueous solution or suspension that the neutral point is reached. The obtained solution can then be evaporated to dryness in a vacuum. Often, it is advantageous to precipitate the formed neutral salts by adding water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

Another object of the invention are agents that contain at least one of the compounds according to the invention.

The invention further relates to a process for the production of these agents, which is characterized in that the dendrimeric polymer complex, dissolved in water, is brought into a form suitable for enteral or parenteral administration with this additives and stabilizers that are commonly used in galenicals, so that the complex is present at a concentration of 0.01 to 1.0 mol/l and preferably at a concentration of 0.1 to 0.5 mol/l. The resulting agents are then optionally sterilized. They are administered, depending on the diagnostic problem, generally at a dose of 0.01–0.3 mmol/kg of body weight.

Suitable additives are, for example, physiologically harmless buffers (such as, e.g., tromethamine or diethylenetriaminepentaacetic acid), small additions of the respective polymeric, dendrimeric complexing agent, optionally in the form of a physiologically compatible salt, such as, e.g., the potassium salt as well as electrolytes, such as, e.g., sodium chloride and/or optionally antioxidants, such as, e.g., ascorbic acid.

In principle, it is also possible to produce the diagnostic agents according to the invention even without isolating the polymeric complex compound. In each case, special care must be taken to undertake the complexing, so that the salts and salt solutions according to the invention are practically free of noncomplexed metal ions that have a toxic effect.

This can be ensured, for example, with the aid of color indicators, such as xylenol orange, by control titrations during the production process. As a last precaution, a purification of the isolated complex salt remains.

Other objects of the invention are characterized by the claims.

The substances according to the invention meet the varied requirements that are to be made on a "blood-pool agent" in NMR diagnosis. The compounds and agents produced from them are distinguished by:

an advantageous elimination kinetics, good compatibility, high effectiveness, which is necessary to load the body with the fewest possible amounts of foreign substances, low osmolality.

In particular, the compounds (or agents) according to the invention remain exclusively in the vascular space during the period of the study, so that a poor definition in the NMR picture, by contrast medium diffusing in the interstitial space, is not observed. Further, the agents according to the invention exhibit not only a high stability in vitro, but also a surprisingly high stability in vivo, so that a release or an exchange of the ions—toxic as such—bound to the complexes, does not take place within the time in which the new contrast media are completely excreted again.

The following example is used for a more detailed explanation of the object of the invention, without intending that it be limited to this object.

The shorthand expression "Diaminobutyl-dendrimer-$(NH_2)_{32}$" used below stands for a dendrimer, which consists of a diaminobutyl nucleus A and 60 reproduction units ($-CH_2-CH_2-CH_2-N <$) with 32 terminal $NH_2$ groups.

EXAMPLE 1 a) [10]-Carboxy-3,6,9-tris(carboxymethyl)-3,6,9-triazadecanoyl] Derivative of the polyaminodendrimer diaminobutyl-dendrimer-$(NH_2)_{32}$ 3.51 g (1 mmol) of the 32-amine that is described in Example VIII of WO 93/14147 is dissolved in 300 ml of water. Then, 36.02 g (96 mmol) of $N^3$-(2,6-dioxomorpholinoethyl)-$N^6$-(ethoxycarbonylmethyl)-3,6-diaza-octanedioic acid (Example 13a of EP 0 331 616) is added in portions in solid form within 2 hours, whereby the pH is maintained at 8.5 by adding 1N NaOH. After the addition of anhydride is completed, the solution is stirred for 2 more hours at pH 11, then adjusted with Amberlite® IR 120 ($H^+$ form) to pH 5 and suctioned off from ion exchanger. The solution is ultrafiltered (AMICON® YM 05-membrane), and the retentate is then freeze-dried.

Yield: 15.6 g $H_2O$ content (Karl Fischer): 9.3%

100 mg of the anhydrous complexing agent complexes (Indicator: xylenol orange) 29.6 mg of $Gd^{3+}$ (degree of population with DTPA>91%)

b) Gd-Complex of [10-carboxy-3,6,9-tris(carboxymethyl)-3,6,9-triazadecanoyl] derivative of the polyaminodendrimer diaminobutyl-dendrimer-$(NH_2)_{32}$ 10.0 g of the complexing agent that is described in the above example is dissolved in 300 ml of $H_2O$ and mixed with 3.41 g of $Gd_2O_3$ (=2.96 g of Gd), stirred for 30 minutes at 80° C., adjusted to pH 7 after cooling, membrane-filtered and freeze-dried.

Yield: 12.5 of light yellow, flocculent lyophilizate $H_2O$ content (Karl Fischer): 8.2%

Gd determination (AAS): 22.9%

Analysis (relative to anhydrous substance): Cld: C 37.08% H 4.80% Gd 24.58% N 10.81% Na 0.22% Fnd: C 37.83% H 5.19% Gd 23.10% N 10.97% Na 0.51%

We claim:

1. A dendrimeric polymer complex of formula I

     (I)

in which

A stands for a nitrogen-containing nucleus of base multiplicity b, in which b is the sum of the free valences of the nitrogen-containing nucleus and is a number from 1 to 8 and X stands for a radical that consists of $$\sum_{k=0}^{n-1} 2^k$$

reproduction units S and $2^n$ imaging radicals Y
in which n is the number of generations and stands for a number 1, 2, 3 or 4, and S stands for a radical of formula II

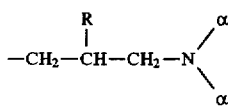     II in which

R stands for a hydrogen atom or a methyl group and the positions α, for generations 0<k<n−1, stand for other reproduction units S, and for the nth generation, stand for imaging radicals Y of formula III or IV.

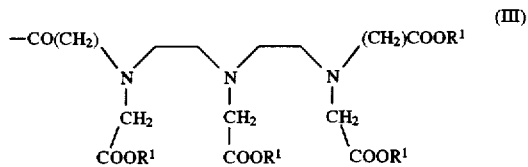     (III)

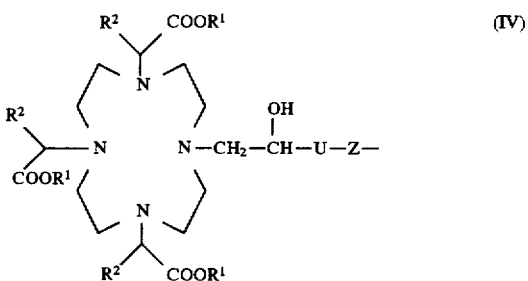     (IV)

in which $R^1$, independently of one another, stand for hydrogen or a metal ion equivalent of the elements of atomic numbers 21–29, 39, 42–44 or 57–83, $R^2$ independently stand for a hydrogen atom, a methyl or an ethyl radical, which optionally is substituted with 1–2 hydroxyl groups, U stands for a straight-chain, branched, saturated or unsaturated $C_1$–$C_{20}$ alkylene group optionally containing imino, phenylene, phelylenoxy, phenylenimino, amide, hydrazide, carbonyl or ester groups, or oxygen, sulfur or nitrogen atoms, or combinations thereof, that are optionally substituted by hydroxy, mercapto, oxo, thioxo, carboxy, carboxyalkyl, ester or amino group(s) or combinations thereof, and Z stands for a CO, NH—CO or NHCS group, whereby the complexes contain at least 8–64 metal ions of the above-mentioned elements and free carboxylic acid groups are present optionally are present as a salt of an inorganic or organic base or amino acid.

2. A dendrimeric polymer complex according to claim 1, wherein nucleus A stands for a nitrogen atom, a radical

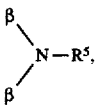

a radical β—N—$(R^5)_2$ or a radical of formula V, VI, VII, or VIII, in which $R^5$ stands for an alkyl, aryl or aralkyl radical with 1 to 12 C atoms that are optionally substituted with 1–4 OH groups, β marks the binding site to radical X, whereby the number of β groups equals the basic multiplicity b, W stands for a straight-chain or branched alkylene, arylene or aralkylene radical with 1 to 12 C atoms, which optionally is interrupted by 1–4 oxygen atoms and optionally substituted by 1–4 hydroxy groups, p stands for the a number 1 to 4, m independently of one another, stand for a number 1 or 2, and r stands for a number 1 to 5.

3. A dendrimeric polymer complex according to claim 1, wherein nucleus A stands for a group>N—$(CH_2)_4$—N<.

4. A diagnostic agent that contains at least one dendrimeric polymer complex according to claim 1 in a physiologically compatible medium, optionally with the additives that are commonly used in galenicals.

5. Process for the production of a dendrimeric polymer complex according to claim 1, which comprises reacting a dendrimeric polymer of formula IX

     (IX)

in which

A and b have the indicated meanings and

X' stands for X, but in contrast to X for the nth generation, the α-positions are not occupied by imaging radicals Y, but by hydrogen atoms, with a reactive precursor of the imaging radical Y in an acylation or addition reaction or with a reactive precursor of a complexing agent of the imaging radical Y, which is then reacted with a metal salt or metal oxide of a metal of the mentioned atomic numbers to provide the imaging radical Y.

6. Process according to claim 5, wherein the reactive precursor contains an activated carboxylic acid, isocyanate or isothiocyanate group for reaction.

7. A dendrimeric polymer complex according to claim 2, wherein nucleus A stands for a group>N—$(CH_2)_4$—N <. acid, isocyanate or isothiocyanate group for reaction.

8. A dendrimeric polymer complex of claim 1, which is the Gd-complex of {10-carboxy-3,6,9-tris(carboxymethyl)-3,6,9-triazadecanoyl} derivative of the polyaminodendrimer diamino-butyl-dendrimer-${\{NH_2\}_{32}}$.

9. A dendrimeric polymer complex of claim 1, wherein A is the residue of an amine of the formula $A(H)_b$, which amine is ammonia, tris-aminoethylamine, 1,4,7,10-tetraazacyclododecane (cyclene), 1,4,7,10,13,16- hexaazacyclooctadecane, 1,3-diaminopropane, 1,4-diaminobutane, 1,5-diaminopentane, 1,12-diamino-4,9-dioxadodecane, 1,4,8,11-tetraazaundecane, 1,5,8,12-tetraazadodecane, 1,5,9,13-tetraazatridecane, diethylenetriamine or triethylenetetramine.

10. A dendrimeric polymer complex of claim 9 wherein the amine is ammonia, tris(2-aminoethyl)amine, diethylenetriamine, cyclene or 1,4-diaminobutane.

11. A method for NMR diagnosis or diagnostic radiology which comprises administering as a contrast agent a dendrimeric polymer complex of claim 1.

12. The method of claim 11, wherein the dendrimeric polymer complex is administered in a dose of 0.01–0.3 mmol/kg of body weight.

* * * * *

UNITED STATES PATENT AND TRADEMARK OFFICE
CERTIFICATE OF CORRECTION

PATENT NO. : 5,759,518
DATED : June 2, 1998
INVENTOR(S) : Heribert SCHMITT-WILLICH et al.

It is certified that error appears in the above-identified patent and that said Letters Patent is hereby corrected as shown below:

In the Claims:
Amend claim 2 as follows:

Line 5, after "VIII" insert the following formulae:

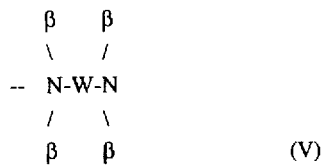

(V)

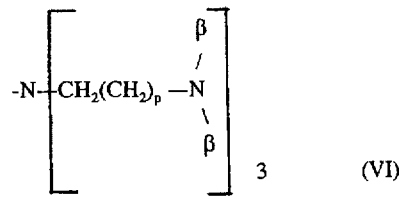

(VI)

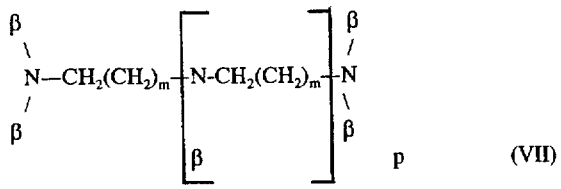

(VII)

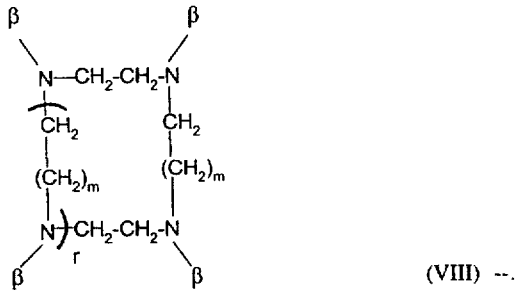

(VIII) --.

Signed and Sealed this

Eleventh Day of April, 2000

*Attest:*

Q. TODD DICKINSON

*Attesting Officer*      *Director of Patents and Trademarks*